United States Patent
Sim et al.

(10) Patent No.: US 9,322,755 B2
(45) Date of Patent: Apr. 26, 2016

(54) CELL CAPTURING FILTER HAVING HIGH ASPECT RATIO

(71) Applicant: Samsung Electronics Co., Ltd., Suwon-si (KR)

(72) Inventors: Tae-seok Sim, Seoul (KR); Min-seoks Kim, Yongin-si (KR); Mi-jeong Song, Suwon-si (KR); Jeong-gun Lee, Seoul (KR); June-young Lee, Anyang-si (KR); Yeon-jeong Kim, Yongin-si (KR); Sang-hyun Baek, Hwaseong-si (KR); Jin-mi Oh, Suwon-si (KR); Hyo-young Jeong, Incheon (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 135 days.

(21) Appl. No.: 13/713,678

(22) Filed: Dec. 13, 2012

(65) Prior Publication Data
US 2013/0149217 A1 Jun. 13, 2013

(30) Foreign Application Priority Data

Dec. 13, 2011 (KR) ......................... 10-2011-0134003
May 21, 2012 (KR) ......................... 10-2012-0053778

(51) Int. Cl.
*G01N 1/34* (2006.01)
*B01L 3/00* (2006.01)
*G01N 1/40* (2006.01)
(Continued)

(52) U.S. Cl.
CPC ............ *G01N 1/34* (2013.01); *B01L 3/502753* (2013.01); *B01L 3/502761* (2013.01); *C12M 33/14* (2013.01); *C12M 47/04* (2013.01); *G01N 1/4077* (2013.01); *B01L 2200/0631* (2013.01); *B01L 2200/0668* (2013.01); *B01L 2300/0681* (2013.01); *B01L 2300/0803* (2013.01);
(Continued)

(58) Field of Classification Search
None
See application file for complete search history.

(56) References Cited

U.S. PATENT DOCUMENTS 5,304,487 A   4/1994 Wilding et al.
6,695,765 B1 * 2/2004 Beebe et al. .................... 600/33
(Continued)

FOREIGN PATENT DOCUMENTS

EP   0 368 241 A2   5/1990
JP   2005-007352 A   1/2005
(Continued)

OTHER PUBLICATIONS

Extended European Search Report by the European Patent Office in Application No. 12196935.6, mailed on Mar. 25, 2013.

*Primary Examiner* — Jill Warden
*Assistant Examiner* — Timothy G Kingan
(74) *Attorney, Agent, or Firm* — Leydig, Voit & Mayer, Ltd.

(57) ABSTRACT

A cell capturing filter, in which cells or particles having a predetermined size or greater in a sample may be easily captured, and clogging of a flow passage due to the captured cells or particles may be prevented, and stresses acting on the captured cells or particles may be reduced, having a first surface and a second substrate having a second surface that is bonded to the first surface, wherein the first substrate may include a flow passage formed in the first surface of the first substrate so that a sample flows in the flow passage, and a barrier that protrudes across the flow passage, and the second substrate may include a fine groove formed in an area on the second surface corresponding to the barrier, and a gap may exist between a surface of the barrier and the fine groove.

10 Claims, 8 Drawing Sheets

(51) Int. Cl.
 *C12M 1/26* (2006.01)
 *C12M 1/00* (2006.01)

(52) U.S. Cl.
 CPC .... *B01L2300/087* (2013.01); *B01L 2300/0816* (2013.01); *B01L 2400/086* (2013.01)

(56) References Cited

U.S. PATENT DOCUMENTS

| | | | |
|---|---|---|---|
| 2002/0197167 A1* | 12/2002 | Kornelsen | 417/53 |
| 2003/0217923 A1* | 11/2003 | Harrison et al. | 204/450 |
| 2004/0096960 A1* | 5/2004 | Burd Mehta et al. | 435/287.2 |
| 2005/0224352 A1* | 10/2005 | Harrison et al. | 204/451 |
| 2005/0229696 A1* | 10/2005 | Takayama | 73/204.26 |
| 2008/0031787 A1 | 2/2008 | Yu | |
| 2008/0318324 A1 | 12/2008 | Chiu et al. | |
| 2009/0042241 A1 | 2/2009 | Yu-Chong et al. | |
| 2010/0323388 A1 | 12/2010 | Chiu et al. | |
| 2011/0065181 A1 | 3/2011 | Hvichia et al. | |

FOREIGN PATENT DOCUMENTS

| | | |
|---|---|---|
| KR | 1020100029181 A | 3/2010 |
| KR | 1020100065538 A | 6/2010 |
| WO | WO 03/008931 A2 | 1/2003 |

* cited by examiner

CELL CAPTURING FILTER HAVING HIGH ASPECT RATIO

CROSS-REFERENCE TO RELATED APPLICATIONS

This application claims the benefit of Korean Patent Application No. 10-2011-0134003, filed on Dec. 13, 2011, and Patent Application No. 10-2012-0053778, filed on May 21, 2012, in the Korean Intellectual Property Office, the disclosure of which is incorporated herein in its entirety by reference.

BACKGROUND

1. Field

The present disclosure relates to cell capturing filters having a high aspect ratio, and more particularly, to cell capturing filters capable of easily capturing cells or particles of a predetermined size or greater in a sample, preventing clogging of a flow passage by the captured cells or particles, and reducing stress applied to the captured cells or particles.

2. Description of the Related Art

Early detection is of vital importance for treating various forms of cancer, and much research is being conducted to find cancer detection methods that are fast, simple, and accurate. Recently, a cancer diagnosis method performed by capturing a circulating tumor cell (CTC) from a blood sample has been suggested. However, it is difficult to capture CTCs due to low concentrations of CTCs in blood, e.g., only one CTC may be found among $10^9$ cells. For instance, with regard to breast cancer, about five or less CTCs may be found in about 7.5 ml of blood, and with regard to large intestine cancer, about three or less CTCs may be found in about 7.5 ml of blood. Thus, for an accurate diagnosis of cancer, the rare CTCs need to be captured without loss. Moreover, CTCs die easily, and thus, capturing needs to be conducted while minimizing adverse conditions to the cells.

Capturing CTCs may be conducted by using a filter that allows erythrocytes and leucocytes in blood to pass through and filters only CTCs. However, this type of filter usually has a structure in which multiple, column-shaped, and complicated patterns are formed in minute flow passages through which blood may flow. While erythrocytes and leucocytes, which have a relatively small size, may pass through these patterns, CTCs which are relatively large may be captured between the patterns. However, the flow passages may be clogged by the captured CTCs. Once clogging occurs, stress is applied to the CTCs and the CTCs may be damaged, and leucocytes may be captured together with the CTCs, which decreases the analysis efficiency and increases the analysis time.

SUMMARY

Provided are filters capable of easily capturing cells or particles having a predetermined size or greater in a sample, preventing clogging of a flow passage by the captured cells or particles, and reducing stress acting on the captured cells or particles.

Additional aspects will be set forth in part in the description which follows and, in part, will be apparent from the description, or may be learned by practice of the presented embodiments.

According to an aspect of the present invention, a filter includes: an inlet through which a sample flows in; an outlet through which a sample flows out; a flow passage having a first surface and a second surface that face each other such that a sample flows between the inlet and the outlet; and a filter unit that is disposed in the flow passage to capture target cells or target particles from a sample flowing through the flow passage, wherein the filter unit includes a barrier that protrudes from the second surface toward the first surface to block the flow passage and a gap that is formed between the barrier and the first surface of the flow passage.

A size of the gap is smaller than the height of the flow path, defined by the distance from the first surface to the second surface, and may be smaller than a size of a target cell or a target particle in a sample.

An aspect ratio of a width of the filter unit and the gap may be at least 1,000:1, wherein the width of the filter unit is a dimension of the filter unit perpendicular to the general direction of flow from the inlet to the outlet.

The barrier may have an inclined sidewall. In other words, the barrier protruding from the second surface is defined in part by a sidewall traversing the flow passage in a direction generally perpendicular to the direction of flow from the inlet to the outlet, and the sidewall is inclined relative to the second surface.

The filter unit may be disposed nearer to the outlet than to the inlet.

The flow passage may include a first end portion connected to the inlet, a second end portion connected to the outlet, and a center portion between the first end portion and the second end portion, wherein the first end portion is tapered and gradually broadens from the inlet toward the center portion, and the second end portion is tapered and gradually narrows from the center portion toward the outlet.

The filter may further include a fluid resistance unit disposed in the flow passage between the filter unit and the inlet.

The filter may further include a micro-channel formed between the fluid resistance unit and the first end portion of the flow passage. More particularly, each of the end portions may comprise a perimeter wall extending between the first surface and the second surface in a generally perpendicular direction to define the sides of the flow path, and the fluid resistance unit is positioned relative to the perimeter wall in the first end portion of the flow path to form micro-channel between the fluid resistance unit and the perimeter wall of the first end portion of the flow passage.

The fluid resistance unit may have a rhombus or diamond shape.

The fluid resistance unit may protrude from the second surface of the flow passage.

According to another aspect of the present invention, a filter includes: a first substrate having a first surface; a second substrate having a second surface that is bonded to the first surface; an inlet and an outlet that are each formed to pass through the first substrate or the second substrate; a flow passage that is formed between the inlet and the outlet by etching the second surface of the second substrate; and a filter unit that is disposed inside the flow passage to capture target cells or target particles from a sample that flows through the flow passage, wherein the filter unit includes: a barrier that protrudes from a bottom surface of the flow passage to block the flow passage; a groove that is formed by etching a portion of the first surface of the first substrate corresponding to the barrier; and a gap that is formed between the groove and the barrier.

A width of the groove may be broader than a width of an upper surface of the barrier.

The filter may further include a fluid resistance unit disposed in a flow passage between the filter unit and the inlet, and an upper surface of the fluid resistance unit and an upper surface of the barrier may be at the same height as the second surface of the second substrate.

According to another aspect of the present invention, a filter includes: an inlet through which a sample flows in; an outlet through which a sample flows out; a flow passage having a first surface and a second surface that face each other such that a sample flows between the inlet and the outlet; and at least two filter units that are disposed in the flow passage to capture target cells or target particles in a sample flowing through the flow passage, wherein the at least two filter units are arranged in parallel in a direction in which a sample flows in the flow passage, and each of the filter units comprises a barrier that is protruded from the second surface to the first surface of the flow passage to block the flow passage and a gap that is formed between the barrier and the flow passage.

According to another aspect of the present invention, a filter includes: a first substrate having a first surface; a second substrate that has a second surface facing the first surface of the first substrate and that is bonded to the first substrate; an inlet that is formed through a center portion of the first substrate or the second substrate; a flow passage that is connected to the inlet and is formed between the first substrate and the second substrate; and a filter unit that is disposed in the flow passage to capture target cells or target particles in a sample flowing through the flow passage, wherein the filter unit is formed along circumferences or perimeters of the first substrate and the second substrate.

The filter unit may include: a barrier protruded from the second surface of the second substrate along the circumference or perimeter of the second surface of the second substrate; a groove that is engraved along the circumference or perimeter of the first surface of the first substrate corresponding to the barrier; and a gap that is formed between the groove and the barrier.

The filter may further include a plurality of isolation layers protruded from the second surface of the second substrate, wherein the plurality of isolation layers are arranged in radial directions with respect to the inlet.

The isolation layers may be each connected to the barrier.

The flow passage may include a plurality of flow passages that are separated from one another by the plurality of isolation layers.

A width of each flow passage formed between two adjacent isolation layers may increase from the inlet toward the barrier.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
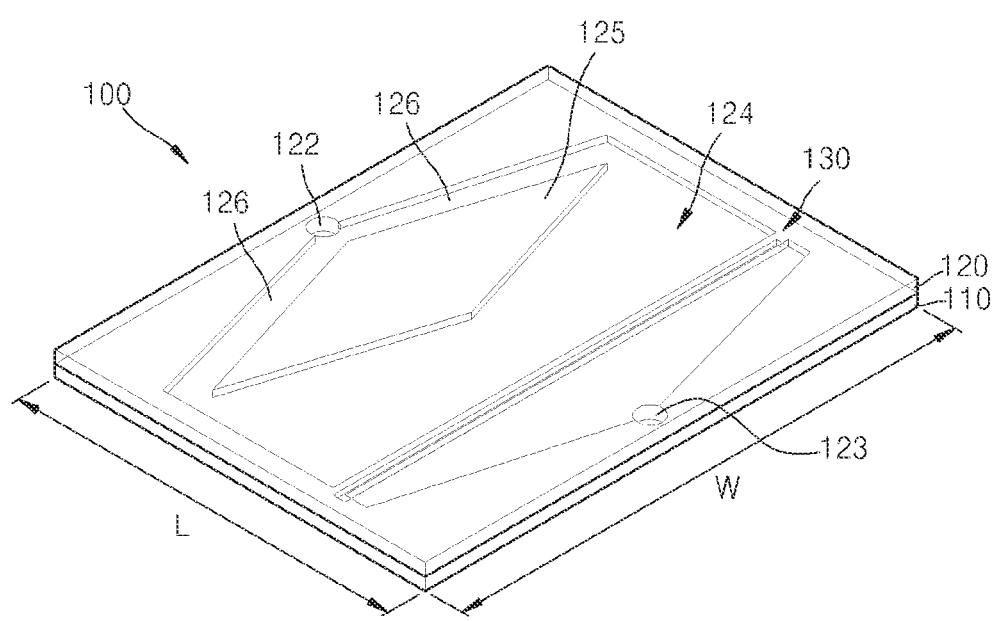
FIG. 1 is a schematic perspective view of a cell capturing filter according to an embodiment of the present invention.

Reference will now be made in detail to embodiments, examples of which are illustrated in the accompanying drawings, wherein like reference numerals refer to the like elements throughout, and sizes of the elements may be exaggerated for clarity and convenience of description. In this regard, the present embodiments may have different forms and should not be construed as being limited to the descriptions set forth herein. Accordingly, the embodiments are merely described below, by referring to the figures, to explain aspects of the present description.

First, FIG. 1 is a schematic perspective view of a cell capturing filter 100 according to an embodiment of the present invention. Referring to FIG. 1, the cell capturing filter 100 includes an inlet 122 through which a sample to be tested flows in, an outlet 123 through which a tested sample is discharged, a flow passage 124 that is formed between the inlet 122 and the outlet 123 such that a sample flows therebetween, and a filter unit 130 that is formed across the flow passage 124 to capture target cells or target particles from the sample that flows through the flow passage 124. As illustrated in FIG. 1, the filter unit 130 may be disposed to be nearer to the outlet 123 than to the inlet 122.

In addition, the cell capturing filter 100 according to the current embodiment of the present invention may further include a fluid resistance unit 125 that is disposed in the flow passage 124 between the inlet 122 and the filter unit 130 to be adjacent to the inlet 122. Due to the fluid resistance unit 125, as illustrated in FIG. 1, a sample that has flown through the inlet 122 flows toward an edge of the flow passage 124 through two, narrow micro-channels 126 that are formed between the fluid resistance unit 125 and an inner wall of the flow passage 124. Then, the sample may flow from the edge to a center of the flow passage 124 as denoted by an arrow in FIG. 7. The fluid resistance unit 125 may control a speed of the sample that has flown into the inlet 122 and distribution of stream lines of the sample. For example, the fluid resistance unit 125 may prevent the sample that has flown in from the inlet 122 from directly flowing into the flow passage 124, thereby reducing a speed of the sample, and may maintain a uniform speed of the sample in a predetermined range in the flow passage 124. Also, the fluid resistance unit 125 may be used to maintain a uniform distribution of stream lines of the sample within the flow passage 124 and maintain similar lengths of each stream line. Accordingly, the sample may flow uniformly along the flow passage 124 by using the fluid resistance unit 125, and concentration of the sample in any predetermined area of the filter unit 130 may be prevented.

As illustrated in FIG. 1, the fluid resistance unit 125 may have a rhombus or diamond shape, but is not limited thereto. For example, the fluid resistance unit 125 may be polygonal such as triangular or rectangular, or circular, oval, or fan-shaped, streamlined, or a form of a combination of these shapes.

Figure 2:
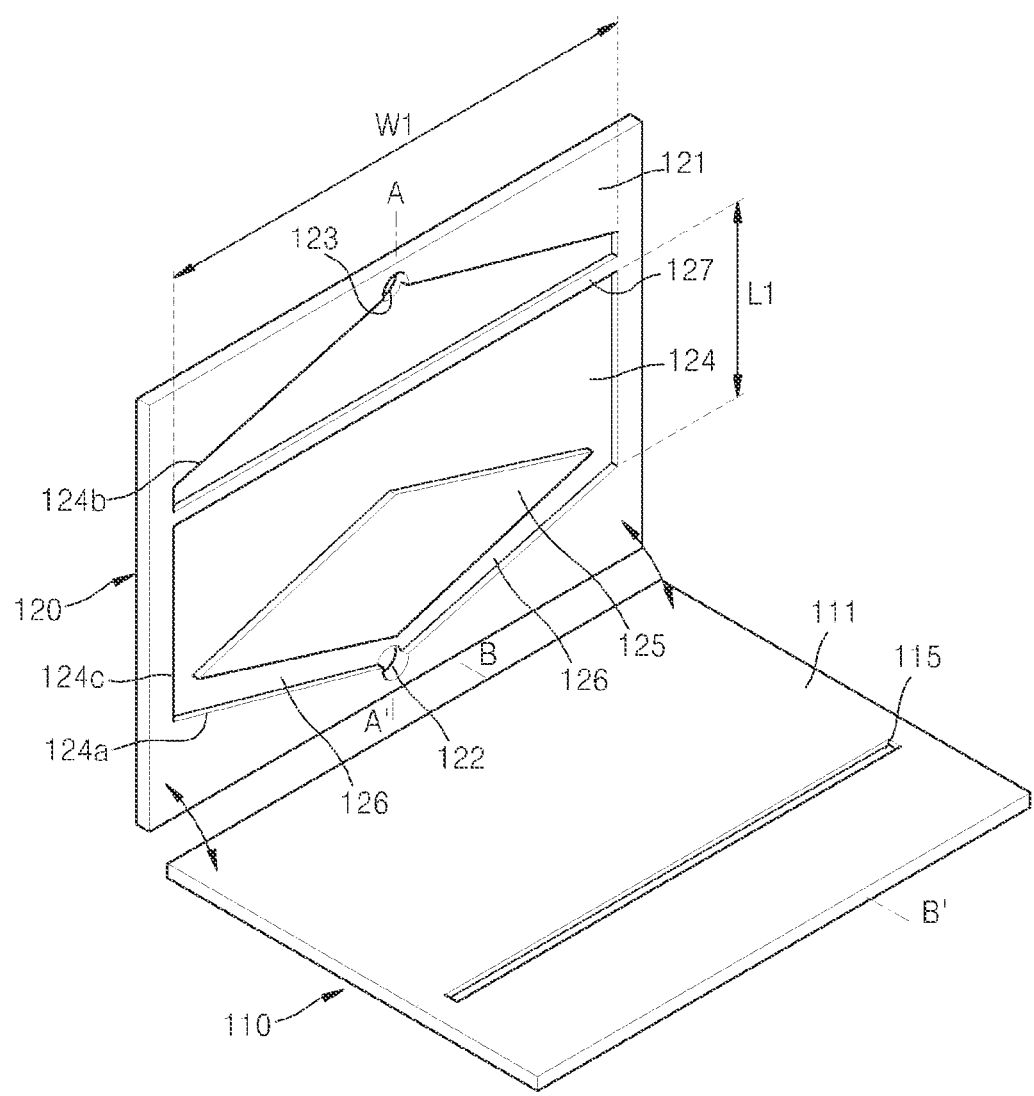
FIG. 2 is a schematic disassembled perspective view of the cell capturing filter of FIG. 1, according to an embodiment of the present invention.

The cell capturing filter 100 according to the current embodiment of the present invention may be formed by bonding two substrates, such as first and second substrates 110 and 120 each having a planar surface and on which the inlet 122, the outlet 123, the flow passage 124, the fluid resistance unit 125, and the filter unit 130 or the like are formed. FIG. 2 is a schematic disassembled perspective view of the cell capturing filter 100 in which structures of surfaces of the first and second substrates 110 and 120 are shown.

Referring to FIG. 2, the first substrate 110 has a planar, first surface 111. The first substrate 110 may have a rectangular form having a width (W) at least twice its length (L). For example, the width (W) of the first substrate 110 may be about 3 cm, and the length (L) thereof may be about 1.5 cm. A fine groove 115 which is a portion of the filter unit 130 may be formed in the first surface 111. The groove 115 may be formed in a straight line that is long, narrow, and extends along a width direction of the first substrate 110. For example, the groove 115 may be formed by etching the first surface 111 of the first substrate 110 by using a wet etching method. The first substrate 110 may be formed of a transparent glass or a transparent plastic material, but is not limited thereto. For example, the first substrate 100 may be formed of a material such as acrylate, polymethylacrylate, polymethylmethacrylate (PMMA), polycarbonate, polystyrene, polyimide, epoxy resin, polydimethylsiloxane (PDMS), or parylene.

Also, the second substrate 120 has a planar, second surface 121. The second substrate 120 may also have the same dimensions, e.g., width (W) and length (L), as the first substrate 110. However, according to necessity, the second substrate 120 may be larger or smaller than the first substrate 110. The second substrate 120 may be formed of a material such as a transparent glass, quartz, plastic, or polymer so that captured cells or particles may be observed through the second substrate 120.

As illustrated in FIG. 2, the inlet 122 and the outlet 123 may be formed to completely pass through the second substrate 120. The flow passage 124 is formed between the inlet 122 and the outlet 123. For example, the flow passage 124 may be formed by etching the second surface 121 using a wet etching method. Also, the fluid resistance unit 125 and a barrier 127 protrude from the bottom of the flow passage 124. For example, the fluid resistance unit 125 and the barrier 127 may be formed by preventing a portion of the second surface 121 from being etched by using a mask (not shown) when etching the second surface 121 to form the flow passage 124. Accordingly, upper surfaces of the fluid resistance unit 125 and the barrier 127 may be coplanar with the second surface 121 of the second substrate 120.

Meanwhile, the flow passage 124 may have a first end portion 124a that is connected to the inlet 122, a second end portion 124b that is connected to the outlet 123, and a center portion 124c between the first end portion 124a and the second end portion 124b. As illustrated in FIG. 2, the first end portion 124a and the second end portion 124b may be tapered. For example, the first end portion 124a may gradually broaden from the inlet 122 toward the center portion 124c. In addition, the second end portion 124b may gradually narrow from the center portion 124c toward the outlet 123. A width W1 of the center portion 124c may be considerably broader than a length L1 thereof. For example, a ratio of the width W1 and the length L1 of the center portion 124c may be 3:1 or greater or 100:1 or less. Thus, a rapid increase in a flux of a sample may be prevented, and a pressure applied to the flow passage 124 may be reduced.

As illustrated in FIG. 2, the fluid resistance unit 125 may be disposed to be nearer to the inlet 122 than to the outlet 123. Also, the fluid resistance unit 125 may be tapered at a similar degree as the first end portion 124a of the flow passage 124. As described above, the fluid resistance unit 125 may be a rhombus or diamond shape or other polygonal shapes. Thus, two, narrow micro-channels 126 may be formed between the fluid resistance unit 125 and the inner wall of the flow passage 124. Two edges of the fluid resistance unit 125 face two inner walls of the flow passage 124, respectively. Accordingly, a sample that enters the inlet 122 may flow along the micro-channels 126, and then may be supplied to the two edges of the flow passage 124. Then, the sample may be uniformly distributed in the center portion 124c of the flow passage 124 to flow toward the outlet 123.

As illustrated in FIG. 2, the barrier 127 may be disposed to be closer to the outlet 123 than to the inlet 122. The barrier 127 is formed in a portion corresponding to the groove 115 formed in the first surface 111 of the first substrate 110. Thus, when the first substrate 110 and the second substrate 120 are bonded, the barrier 127 and the groove 115 may face each other. Like the groove 115, the barrier 127 may also be formed in a narrow, straight line extending along a width direction of the second substrate 120. The barrier 127 may be disposed across the entire width of the flow passage 124 to block the flow passage 124.

Figure 3:
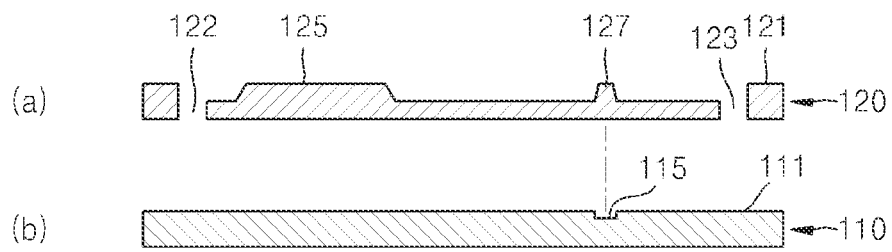
FIG. 3 is a schematic cross-sectional view of two substrates of the cell capturing filter illustrated in FIG. 1.

FIG. 3 is a schematic cross-sectional view of the two substrates 110 and 120 of the cell capturing filter 100 illustrated in FIG. 1 having the above-described structure. In detail, an upper portion (a) of FIG. 3 is a cross-sectional view of the second substrate 120 cut along a line A-A' (FIG. 2), and a lower portion (b) of FIG. 3 is a cross-sectional view of the first substrate 110 cut along a line B-B' (FIG. 2). Referring to (a) of FIG. 3, the inlet 122 and the outlet 123 are formed through the second substrate 120, and the flow passage 124 is formed between the inlet 122 and the outlet 123. In addition, the fluid resistance unit 125 and the barrier 127 protrude from a bottom surface of the flow passage 124 in the flow passage 124. Heights of the fluid resistance unit 125 and the barrier 127 may be the same as the height of the second surface 121. That is, the surfaces of the fluid resistance unit 125 and the barrier 127 may be coplanar with the second surface 121. Also, referring to (b) of FIG. 3, the fine groove 115 may be formed in a portion of the first surface 111 of the first substrate 110 corresponding to the barrier 127.

Figure 4:
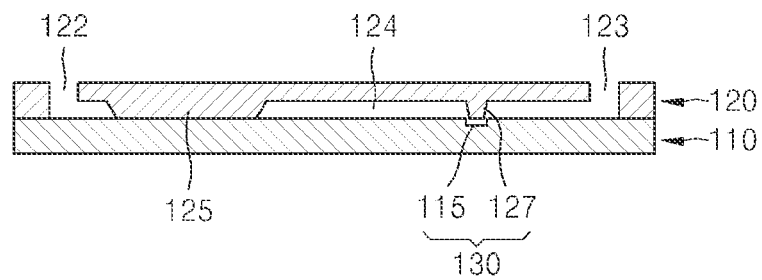
FIG. 4 is a schematic cross-sectional view illustrating the two substrates illustrated in FIG. 3 that are bonded to each other.

FIG. 4 is a schematic cross-sectional view illustrating the first and second substrates 110 and 120 that are bonded to each other. Referring to FIG. 4, the first surface 111 of the first substrate 110 and the second surface 121 of the second substrate 129 may face each other and be bonded to each other. Thus, the entire area of the upper surface of the fluid resistance unit 125 may contact the first surface 111 of the first substrate 110. On the other hand, as the groove 115 is formed in the first surface 111 of the first substrate 110, a fine gap exists between the barrier 127 and the groove 115. A size of the gap may be determined by a depth of the groove 115. For example, the size of the gap may be smaller than a diameter of target cells or target particles to be captured. That is, the depth of the groove 115 formed in the first surface 111 of the first substrate 110 may be smaller than the diameter of target cells or target particles to be captured. Also, a width of the groove 115 may be broader than a width of an upper surface of the barrier 127 in consideration of an alignment error of the first substrate 110 and the second substrate 120. The groove 115 and the barrier 127 form the filter unit 130 of the cell capturing filter 100.

Figure 5:
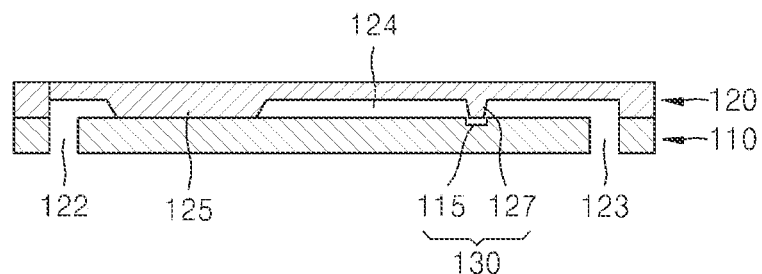
FIG. 5 is a schematic cross-sectional view illustrating a cell capturing filter according to an embodiment of the present invention.

Although the inlet 122 and the outlet 123 are formed in the second substrate 120 in FIGS. 2 through 4, the embodiment of the present invention is not limited thereto. FIG. 5 is a schematic cross-sectional view illustrating a cell capturing filter according to another embodiment of the present invention. As illustrated in FIG. 5, according to another embodiment, the inlet 122 and the outlet 123 may be formed not through the second substrate 120 but through the first substrate 110. That is, the flow passage 124, the fluid resistance unit 125, and the barrier 127 may be formed in the second substrate 120, and the inlet 122, the outlet 123, and the groove 115 may be formed in the first substrate 110.

Figure 6:
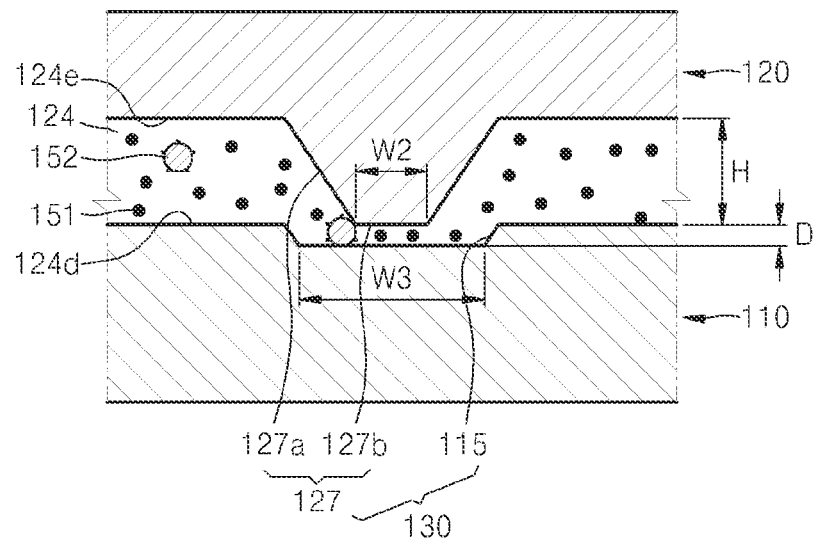
FIG. 6 is a schematic partial cross-sectional view illustrating an operation of the cell capturing filter illustrated in FIG. 1.

FIG. 6 is a schematic partial cross-sectional view illustrating an operation of the cell capturing filter 100 illustrated in FIG. 1, wherein only the filter unit 130 is shown. Referring to FIG. 6, the barrier 127 and the groove 115 are facing each other, and the groove 115 has a predetermined depth D. Accordingly, a gap corresponding to the depth of the groove 115 may be formed between an upper surface 127b of the barrier 127 and the bottom of the groove 115. The gap may be, for example, about 8 μm, in case CTCs are to be captured. Also, as illustrated in FIG. 6, a width W3 of the bottom of the groove 115 may be greater than a width W2 of the upper surface 127b of the barrier 127. Accordingly, when bonding the first substrate 110 and the second substrate 120, there is no need to precisely align the first substrate 110 and the second substrate 120. Even when there is a slight alignment error, the barrier 127 may be disposed quite accurately in the groove 115, and thus, the upper surface 127b of the barrier 127 may not directly contact the first surface 111 of the first substrate 110.

Meanwhile, a sidewall 127a of the barrier 127 needs not be perpendicular to the bottom of the flow passage 124 but instead may be inclined. Thus, there is no need to form the barrier 127 using a method such as a deep reactive ion etching (DRIE) method. In some cases, a wet etching method can be used to achieve the barrier 127. Likewise, the groove 115 may also be formed using a wet etching method. Thus, the manufacturing process of the cell capturing filter 100 may be simplified and the manufacturing time and the manufacturing costs may be reduced.

Referring to FIG. 6, it is assumed that the left side (of the drawing) is directed to the inlet 122, and the right side (of the drawing) is directed to the outlet 123. For example, when a blood sample flows in through the inlet 122, the blood sample flows toward the outlet 123 along the flow passage 124. The flow passage 124 may have a first surface 124d formed by the first substrate 110 and a second surface 124e formed by the second substrate 120. In other words, the flow passage may be defined, at least in part, by a surface of the first substrate and a surface of the second substrate, the substrates (and their respective surfaces) positioned to face one another. A height H of the flow passage 124, that is, a gap between the first surface 124d and the second surface 124e facing each other, may be, for example, about 30 μm~500 μm (e.g., about 50 μm) so that a blood sample may easily flow therebetween. To this end, the second surface 121 of the second substrate 120 may be etched to a depth of about 30 μm~500 μm (e.g., about 50 μm). As described above, the filter unit 130 that is formed by the barrier 127 and the groove 115 and has a fine gap is disposed inside the flow passage 124. For example, the barrier 127 protrudes from the second surface 124e toward the first surface 124d, and a gap is formed between the barrier 127 and the first surface 124d. Accordingly, while a blood sample flows through the flow passage 124 toward the outlet 123, the blood sample passes through the filter unit 130. As illustrated in FIG. 6, erythrocytes 151 in the blood sample have flat disk shapes having a diameter of about 7 μm to about 8 μm and a thickness of about 1 μm to about 2 μm and thus may pass through the filter unit 130. However, CTCs 152 having a diameter of about 20 μm, which is larger than the gap, are not able to pass through the gap and thus may be captured by the filter unit 130.

Figure 7:
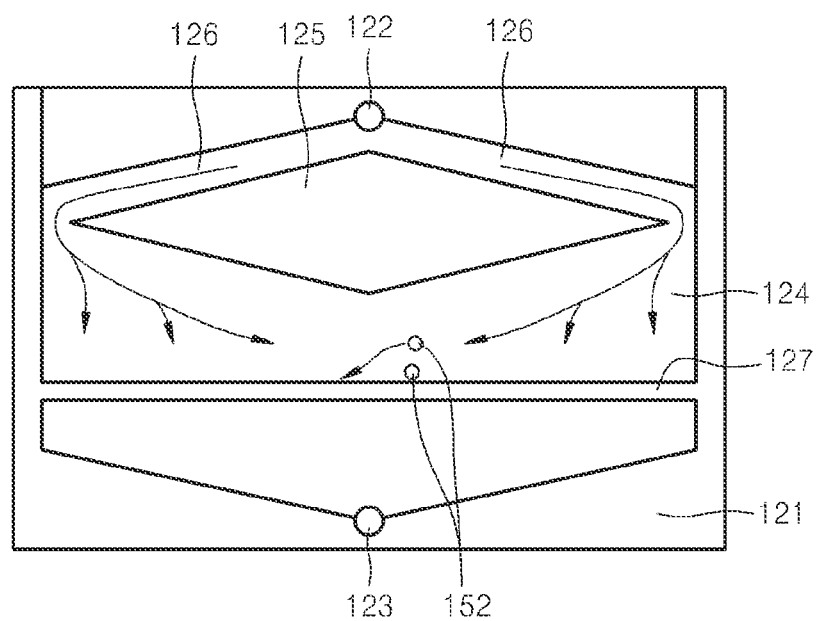
FIG. 7 is a schematic plan view illustrating an operation of the cell capturing filter illustrated in FIG. 1.

According to the cell capturing filter 100 of the current embodiment of the present invention, the filter unit 130 has a very large aspect ratio, and thus even when target cells or other target particles such as the CTCs 152 are captured, the filter unit 130 may not be clogged. FIG. 7 is a schematic plan view illustrating an operation of the cell capturing filter 100 illustrated in FIG. 1. Referring to FIG. 7, a blood sample supplied from the inlet 122 flows through the micro-channels 126 formed by the fluid resistance unit 125 toward the edges of the flow passage 124. Then, the blood sample flows uniformly from the edges toward a center portion of the flow passage 124, thereby flowing to the outlet 123. The barrier 127 is disposed in front of the outlet 123. A width of the barrier 127 is the same as a width of the flow passage 124, and thus, the barrier 127 completely blocks the flow passage 124. Accordingly, the CTCs 152 in the blood sample are caught by the barrier 127 while flowing through the flow passage 124.

As described above, the gap between the upper surface 127b of the barrier 127 and the bottom of the groove 115 may be about 8 μm, and the width of the barrier 127 may be about 3 cm, and thus, an aspect ratio of the filter unit 130 is very large, about 30,000:8. The aspect ratio of 30,000:8 is an example, and the actual aspect ratios may vary according to target types or examination environments but may be about 1,000:1 or higher. Thus, even when the CTCs 152 block some portions of the barrier 127, there is enough spare space for a blood sample to still pass the barrier 127. As a result, damage of the captured CTCs 152 due to stresses generated as a plurality of CTCs 152 are concentrated on any particular position on the barrier 127 is minimized. In addition, even when a plurality of CTCs 152 are caught in many portions on the barrier 127, an increase in flux or hydraulic pressure due to the catching is not large, and thus damage of the captured CTCs 152 due to stresses caused by the increase in flux or hydraulic pressure is minimized. For example, a maximum number of CTCs 152 captured in each blood sample test is about 100, and considering the diameter of the CTCs 152 (about 20 μm) and the width of the flow passage 124 (e.g., about 3 cm), the width of the flow passage 124 that is reduced by the captured CTCs 152 does not greatly affect the flux or hydraulic pressure of the blood sample.

In addition, the captured CTCs 152 may be easily observed by using the cell capturing filter 100 according to the current embodiment of the present invention. Whether CTCs 152 are captured or not or the number of the captured CTCs 152 may be observed along edges of the barrier 127, which have simple linear forms, by using a microscope. Since the second substrate 120 is formed of a transparent material, the cell capturing filter 100 may be directly placed on a stage of a microscope for observation.

Figure 8:
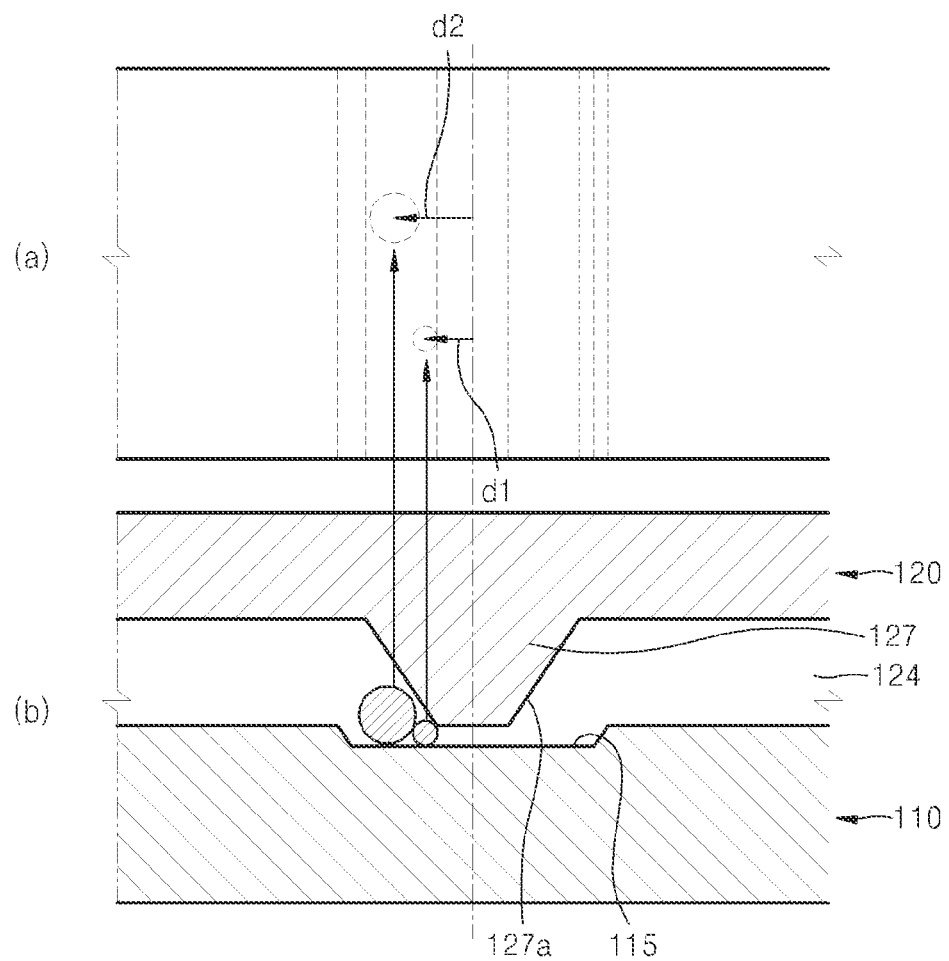
FIG. 8 illustrates a schematic partial cross-sectional view and a schematic partial plan view of an operation of the cell capturing filter illustrated in FIG. 1.

FIG. 8 illustrates a schematic partial cross-sectional view and a schematic partial plan view of an operation of the cell capturing filter 100 illustrated in FIG. 1. As illustrated in FIG. 8, as a sidewall 127a of the barrier 127 is inclined in the cell capturing filter 100, diameters of cells captured by the filter unit 130 may be determined. That is, the greater the sizes of cells, the farther from a central line of the barrier 127 the cells will generally be. Accordingly, the diameters of captured cells may be roughly calculated based on distances d1 and d2 between the cells and the central line of the barrier 127, and types of the cells may be identified based on the diameters.

Figure 9:
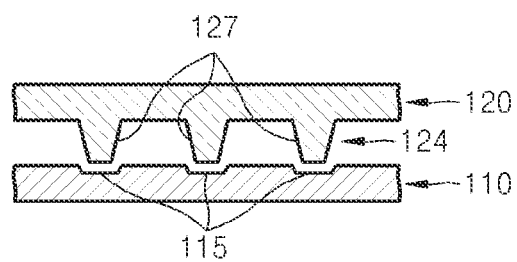
FIG. 9 is a partial cross-sectional view of a filter unit of a cell capturing filter according to another embodiment of the present invention.

While the cell capturing filter 100 including one filter unit 130 including one barrier 127 and one groove 115 has been described, a plurality of filter units 130 respectively including a plurality of barriers 127 and a plurality of grooves 115 may also be formed. FIG. 9 is a partial cross-sectional view of a filter unit 130 of a cell capturing filter 100 according to another embodiment of the present invention.

Referring to FIG. 9, a plurality of parallel barriers 127 are formed on a surface of a second substrate 120 along a direction in which a sample flows in a flow passage 124, and a plurality of parallel grooves 115 respectively facing the barriers 127 are formed on a surface of a first substrate 110. While FIG. 9 illustrates three barriers 127 and three grooves 115, this is an example. According to necessity, two barriers 127 and two grooves 115 may be formed, or four or more barriers and four or more grooves 115 may be formed. According to the current embodiment of the present invention, by disposing the filter units 130 in multiple stages, a capturing rate of target cells or target particles in a sample may be improved. That is, target cells or target particles that have passed through the barrier 127 in the foremost portion with respect to the direction in which a sample flows may be captured by the next barrier 127.

Figure 10:
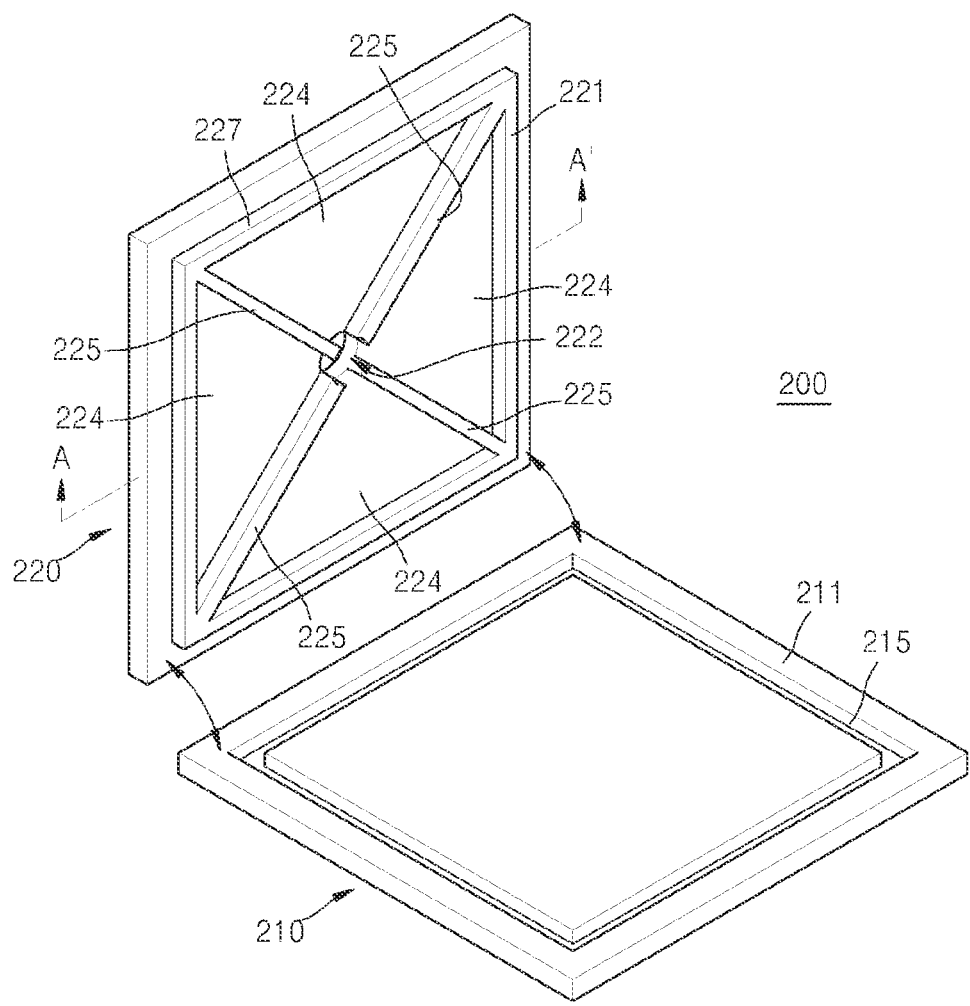
FIGS. 10 and 11 are schematic exploded perspective views illustrating a cell capturing filter according to an embodiment of the present invention.
Figure 11:
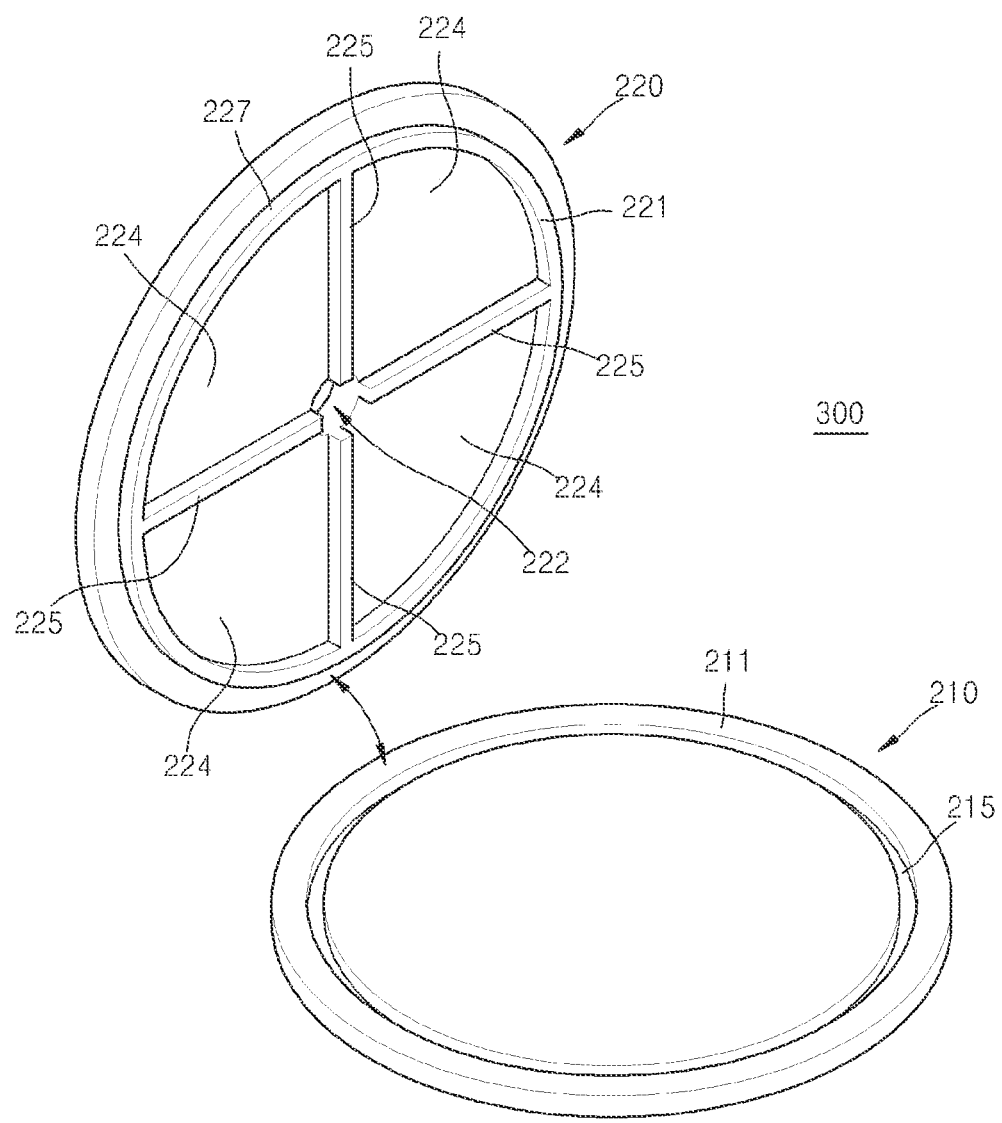

Meanwhile, while the filter unit 130 is described as being disposed on only a surface of the cell capturing filter 100, the embodiments of the present invention are not limited thereto. For example, FIGS. 10 and 11 are schematic exploded perspective views illustrating cell capturing filters 200 and 300 according to other embodiments of the present invention. First, the cell capturing filter 200 having a tetragonal shape includes filter units 215 and 227 on all four sides thereof. In addition, the cell capturing filter 300 having a circular shape illustrated in FIG. 11 includes circular filter units 215 and 227. However, the shapes of the cell capturing filters 200 and 300 illustrated in FIGS. 10 and 11 are examples, and cell capturing filters having polygonal shape such as a triangular shape or a pentagonal shape may also be formed. According to the current embodiment of the present invention, as the filter units 215 and 227 are formed around the entire circumference or perimimeter of the cell capturing filters 200 and 300, an aspect ratio of the filter units 215 and 227 may be further increased.

Referring to FIG. 10, the cell capturing filter 200 may include a first substrate 210 having a flat first surface 211 and a second substrate 220 having a flat second surface 221. The first substrate 210 and the second substrate 220 may be bonded such that the first surface 211 and the second surface 221 face each other. The fine grooves 215 are engraved along a circumference or perimeter of the first surface 211 and are formed in the first surface 211 of the first substrate 210. Also, the barriers 227 are formed protruded from the second surface 221 along a circumference or perimeter of the second surface 221 of the second substrate 220. When bonding the first substrate 210 and the second substrate 220, the grooves 215 and the barriers 227 may be disposed to face each other. Accordingly, a minute gap corresponding to a depth of the grooves 215 is formed between the barriers 227 and the grooves 215. Considering alignment error of the first substrate 210 and the second substrate 220, a width of the grooves 215 may be greater than a width of the barriers 227.

Also, an inlet 222 that passes through a center of the second substrate 220 may be formed. Also, a plurality of isolation layers 225 that extend from the inlet 222 in diagonal directions of the second substrate 220 may be formed. Each of the isolation layers 225 may be connected to the barriers 227 near vertexes of the second substrate 220. A flow passage 224 that is connected to the inlet 222 and in which a sample flows may be formed between two adjacent isolation layers 225. Accordingly, a plurality of flow passages 224 that are separated from one another by the plurality of isolation layers 225 disposed in radial directions with respect to the inlet 222 may be formed. A width of each of the flow passages 224 increases from the inlet 222 toward the barriers 227. A sample provided through the inlet 222 is distributed into and flows through each of the plurality of flow passages 224, and as the width of the flow passages 224 increases gradually along a direction in which the sample flows, the sample may be uniformly distributed in the flow passages 224. In the cell capturing filter 200 illustrated in FIG. 10, an additional outlet is not included, and the sample may be finally discharged through edges of the cell capturing filter 200.

Figure 12:
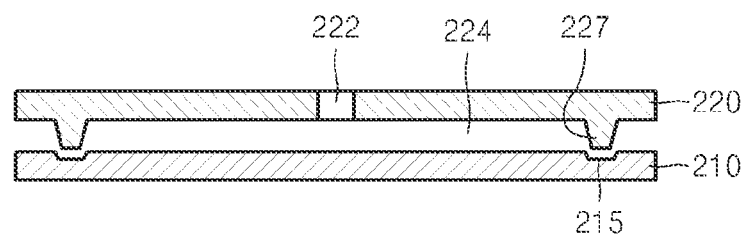
FIG. 12 is a schematic cross-sectional view illustrating the cell capturing filter of FIG. 10.

FIG. 12 is a schematic cross-sectional view of the cell capturing filter 200 illustrated in FIG. 10 along a direction A-A' of FIG. 10. Referring to FIG. 12, the grooves 215 formed in the first substrate 210 and the barriers 227 protruding from the second substrate 220 are disposed to face each other. Referring to the cross-sectional view of FIG. 12, filter units formed of the barriers 227 and the grooves 215 at two end portions of the cell capturing filter 200 are illustrated. The flow passages 224 are formed between the two filter units and between the first substrate 210 and the second substrate 220. Although not illustrated in FIG. 12, a surface of the isolation layers 225 protruding from the second substrate 220 is bonded to a surface of the first substrate 110, and the flow passages 224 may be separated into several areas. In addition, while FIGS. 10 and 12 illustrate the inlet 222 connected to the flow passages 224 and passing through the second substrate 220, the inlet 222 may also be formed through the first substrate 210 as in the embodiment of FIG. 5.

The detailed structure of the cell capturing filter 200 described above with reference to FIGS. 10 and 12 may also be applied to the cell capturing filter 300 illustrated in FIG. 11. The cell capturing filter 300 illustrated in FIG. 11 is different only in its circular shape. Also, the cell capturing filters 200 and 300 illustrated in FIGS. 10 and 11 may also include a filter unit formed in multiple stages as illustrated in FIG. 9.

It should be understood that the example embodiments described herein should be considered in a descriptive sense only and not for purposes of limitation. Descriptions of features or aspects within each embodiment should typically be considered as available for other similar features or aspects in other embodiments.

What is claimed is:

1. A filter comprising:
   a first substrate having a first surface;
   a second substrate having a second surface bonded to the first surface;
   an inlet configured to accept a sample;
   an outlet configured to expel the sample;
   a flow passage disposed in the second surface such that the sample flows between the first and second surfaces from the inlet to the outlet; and
   a filter unit disposed in the flow passage to capture target cells or target particles from the sample flowing through the flow passage,
   wherein the filter unit comprises a barrier protruding from the second surface toward the first surface and a groove formed in a portion of the first surface corresponding to the barrier, the barrier and the groove forming a gap to narrow the flow passage, wherein the flow passage comprises a first end portion fluidly connected to the inlet, a second end portion fluidly connected to the outlet, and a center portion between the first end portion and the second end portion,
further comprising a fluid resistance unit disposed in the flow passage between the filter unit and the inlet, wherein the fluid resistance unit is positioned relative to a perimeter wall in the first end portion of the flow passage to form micro-channels between the fluid resistance unit and the perimeter wall of the first end portion of the flow passage.

2. The filter of claim 1, wherein the gap is smaller than a size of the target cell or the target particle in the sample.

3. The filter of claim 1, wherein an aspect ratio of a width of the filter unit to the gap is at least 1,000:1.

4. The filter of claim 1, wherein the barrier has a sidewall traversing the flow passage in a direction generally perpendicular to the direction of flow from the inlet to the outlet, and the sidewall is inclined relative to the second surface.

5. The filter of claim 1, wherein the filter unit is disposed nearer to the outlet than to the inlet.

6. The filter of claim 1,
wherein the first end portion is tapered and gradually broadens from the inlet toward the center portion, and
the second end portion is tapered and gradually narrows from the center portion toward the outlet,
each of the end portions comprising a perimeter wall extending between the first surface and the second surface in a generally perpendicular direction to define the sides of the flow passage.

7. The filter of claim 1, wherein the fluid resistance unit has a rhombus or diamond shape.

8. The filter of claim 1, wherein the fluid resistance unit protrudes from the second surface of the flow passage.

9. The filter of claim 1 comprising:
at least two filter units disposed in the flow passage to capture target cells or target particles in a sample flowing through the flow passage,
wherein each of the filter units comprises a barrier protruding from the second surface toward the first surface of the flow passage and a groove formed in a portion of the first surface corresponding to the barrier, the barrier and the groove forming a gap to narrow the flow passage;
wherein each barrier traverses the flow passage in a direction generally perpendicular to the overall direction of flow from the inlet to the outlet;
and wherein each of the filter units are arranged parallel to one another.

10. A filter comprising:
an inlet configured to accept a sample;
an outlet configured to expel the sample;
a flow passage having a first surface and a second surface that face each other such that the sample flows between the first and second surfaces from the inlet to the outlet; and
a filter unit disposed in the flow passage to capture target cells or target particles from the sample flowing through the flow passage,
wherein the filter unit comprises a barrier protruding from the second surface toward the first surface and a groove formed in a portion of the first surface corresponding to the barrier, the barrier and the groove forming a gap to narrow the flow passage,
wherein the flow passage comprises a first end portion fluidly connected to the inlet, a second end portion fluidly connected to the outlet, and a center portion between the first end portion and the second end portion,
wherein the first end portion is tapered and gradually broadens from the inlet toward the center portion and the second end portion is tapered and gradually narrows from the center portion toward the outlet, each of the end portions comprising a perimeter wall extending between the first surface and the second surface in a generally perpendicular direction to define the sides of the flow passage, and
further comprising a fluid resistance unit disposed in the flow passage between the filter unit and the inlet, wherein the fluid resistance unit is positioned relative to the perimeter wall in the first end portion of the flow passage to form micro-channels between the fluid resistance unit and the perimeter wall of the first end portion of the flow passage.

* * * * *